(12) United States Patent
Kay et al.

(10) Patent No.: US 6,344,480 B1
(45) Date of Patent: Feb. 5, 2002

(54) ORAL ANALGESIC COMPOSITIONS

(75) Inventors: Martha Francine Kay, Marlton; Teresa Ruth Ratnaraj, Sicklerville, both of NJ (US); Patricia Lynn Sandler, Media, PA (US)

(73) Assignee: American Home Products Corporation, Madison, NJ (US)

( * ) Notice: Subject to any disclaimer, the term of this patent is extended or adjusted under 35 U.S.C. 154(b) by 310 days.

(21) Appl. No.: 08/953,146

(22) Filed: Oct. 17, 1997

(51) Int. Cl.$^7$ ................................................. A61K 31/24
(52) U.S. Cl. ....................................................... 514/535
(58) Field of Search ......................................... 514/535

(56) References Cited

U.S. PATENT DOCUMENTS

| | | | |
|---|---|---|---|
| 4,241,048 A | * 12/1980 | Durbak et al. ................ | 424/45 |
| 5,081,158 A | 1/1992 | Pomerantz .................. | 514/781 |
| 5,446,063 A | * 8/1995 | Reuter et al. ................ | 514/535 |
| 5,547,657 A | * 8/1996 | Singleton et al. ............. | 424/49 |

OTHER PUBLICATIONS

The Merek Index, 11$^{th}$ ed., p. 176 å1138, 1989.*
Allwood et al Soc. Appl. Bacteriol. Tech. Ser, 22, 197–20 (Abstract), 1987.*
Remington's Pharmaceutica Sciences, 15$^{th}$ ed, p. 1891, 1975.*
DiColo et al, Farmaco, Ed. Prat., 38 (9) 323–33 (Abstract), 1983.*
Sumitomo Chemical Co., JP 59176216 A2 (Abstract), 1984.*

* cited by examiner

Primary Examiner—James H. Reamer
(74) Attorney, Agent, or Firm—Steven H. Flynn

(57) ABSTRACT

Alkanol flee glycol based oral analgesic compositions are provided, protected against microbiological degradation by a preservative agent which is a combination of methylparaben and phenylcarbiniol.

10 Claims, No Drawings

ORAL ANALGESIC COMPOSITIONS

BACKGROUND OF THE INVENTION

1. Field of the Invention

This invention relates to oral alkanol free glycol based analgesic compositions containing high concentrations of benzocaine. More particularly, this invention relates to oral analgesic compositions in liquid and gel form having high potency and protected from microbiological degradation by a preservative agent which is a combination of methylparaben and phenylcarbinol.

2. Description of Related Art

An anesthetic composition comprising high concentrations of benzocaine is described in U.S. Pat. No. 5,446,063. The benzocaine is dispersed or suspended in an admixture of water and emollient vehicle and is not completely dissolved. Another benzocainie composition comprising high concentrations of benzocaine is described in U.S. Pat. No. 4,241,048. That patent discloses a composition containing benzocaine suspended in an essentially anhydrous carrier also containing a crystal growth suppressing agent. These prior art patents disclose the use of preservatives including methylparaben and propylparaben.

SUMMARY OF THE INVENTION

According to this invention, an oral analgesic glycol based composition which is anhydrous and alkanol free, containing high concentrations of benzocaine, is provided in liquid or gel form and which is protected from bacterial degradation by a preservative agent which is a combination of methylparaben and phenylcarbinol. The benzocaine compositions of the invention contain about 5 to about 20% by weight of benzocaine, based on the weight of the total composition. The amount of glycol based solvent system is about 40% to about 80% by weight based on the weight of the total composition when in liquid form, and about 40% to about 60% when in gel form. The glycol based solvent system contains about 80% to about 100% by weight of polyethylene glycol when in liquid form and in gel form, based on the weight of the glycol based solvent system, and advantageously up to about 20% by weight of a co-solvent for the benzocaine compatible with polyethylene glycol, based on the weight of the glycol based solvent system. The methylparaben component of the preservative agent can be about 0.05 to about 0.2% by weight of the total composition and the phenylcarbinol component of the preservative agent can be about 0.25 to about 0.5% by weight of the total composition. Co-solvents for the benzocaine compatible with polyethylene glycol are propylene glycol and glycerine.

DETAILED DESCRIPTION OF THE INVENTION

The invention includes analgesic compositions in liquid form and in gel form and in regular strength and maximum strength. The regular strength forms contain about 7.5% to about 10% by weight of benzocaine and the maximum strength forms contain about 10% to about 20% by weight of benzocaine.

The liquid form of the invention can contain in addition to the benzocaine, the glycol based solvent system, and the preservative agent, sweeteners such as saccharin, flavoring agents such as spearmint and coloring agents.

The gel form of the invention contains in addition to the benzocaine, the glycol based solvent system, and the preservative agent, a thickening agent such as Carbomer 934 P brand of carboxy-vinyl polymer, and a co-solvent for the thickening agent such as gylcerin. The thickening agent can range from about 2% to about 2.5% by weight and the co-solvent for the thickening agent can range from about 16% to about 24% by weight of the total composition. Other suitable thickening agents include hydroxyethyl cellulose NF, hydroxypropyl cellulose NF, hydroxypropyl methyl cellulose USP, and polyethylene oxides MW 200,000 to 7 million.

The benzocaine, preservative agents and glycol solvent agents are commercially available in NF or USP grades. The glycerin is commercially available in NF grades containing up to 4% water and the taste of the final gel product is better using the 96% glycerin.

The polyethylene glycol component of the glycol solvent system can range from PEG 400 to PEG 600. Below about PEG 400, the polyethylene glycol does not dissolve the benzocaine with ease, and above about PEG 600, the polyethylene glycol is a waxy solid and difficult to work with.

The preparation of the formulation of the invention is illustrated in the following examples. In the examples, the polyethylene glycol PEG 400 was the commercial NF grade and Carbomer 934 P brand of carboxy-vinyl polymer was that of BF Goodrich.

EXAMPLE 1

The following ingredients were incorporated into the analgesic maximum strength liquid composition of this invention.

| Ingredient | Weight % | Grams Per 500 Grams |
| --- | --- | --- |
| PEG 400 | 10.0 | 50.0 |
| Propylene Glycl | 10.0 | 50.0 |
| Saccharin | 0.177 | 0.885 |
| PEG 400 | 50.8 | 254 |
| Benzocaine | 17.7 | 88.5 |
| Methylparaben | 0.177 | 0.885 |
| Phenylcarbinol | 0.442 | 2.21 |
| N & A Spearmint Flavor | 0.708 | 3.54 |
| PEG 400 | 10.0 | 50.0 |
| Yellow #10 | 0.0106 | 0.0530 |
| Red #40 | 0.0106 | 0.0530 |
| Blue #1 | 0.000221 | 0.0011 |
| Total | 100 | 500 |

The ingredients were mixed in accordance with the following procedure:

Into a 150 ml. beaker were placed 50 grams each of PEG 400 and propylene glycol and the mixture was stirred and heated to 70–75° C. The saccharin was added to the heated solution which was then cooled to 25–30° C. Into a second container were placed 254 grams of PEG 400 and the benzocaine was added with stirring until the benzocaine had dissolved. Into a third container were placed 100 grams of PEG 400 and the dyes were added with stirring until dissolved.

To the benzocaine solution in the second container was added the saccharin solution from the first container and mixed well. The methyl paraben was then added to the second container with stirring until dissolved. The phenylcarbinol was then added to the second container and stirred until dissolved. Next, the flavors were added and then the dye solution from the third container.

The product was a uniform liquid at room temperature with no crystallization and no precipitation. The product is bitter but does not have a bitter after taste.

EXAMPLE 2

The following ingredients were incorporated into the analgesic regular strength liquid composition of this invention.

| Ingredient | Weight % | Grams Per 10 K |
|---|---|---|
| PFG 400 NF | 70.6 | 7060. |
| Propylene Glycol USP | 8.93 | 893.0 |
| Saccharin NF | 0.223 | 22.3 |
| Benzocaine USP | 8.93 | 893. |
| Methylparaben NF | 0.179 | 17.9 |
| Phenylcarbinol NF | 0.446 | 44.6 |
| N & A Spearmint Flavor | 0.714 | 71.4 |
| PFG 400 NF | 10.0 | 1000.0 |
| D & C Red #33 | 0.000446 | 0.0446 |
| FD & C Blue #1 | 0.0000621 | 0.00621 |
| FD & C Yellow #6 | 0.00104 | 0.104 |
| D & C Yellow 10 | 0.00402 | 0.402 |
| Total | 100 | 1003 |

The ingredients were mixed in accordance with the following procedure.

Into a 15 kilogram stainless steel kettle fitted with a Lightnin' mixer were added 7060 g of PEG 400 and 893 g of propylene glycol. The mixer was turned on to form a vortex. The saccharin was added and mixed for 25 minutes. The benzocaine was slowly sprinkled into the vortex and stirred for 50 minutes until completely dissolved. Concurrently, 1000 g of PEG 400 were placed into a 1200 ml stainless steel beaker fitted with a Lightnin' mixer which was turned on to form a vortex. The dyes were sequentially added and mixed until dissolved.

When benzocaine is completely dissolved in first container, add the methylparaben and when dissolved add to the phenylcarbinol and then the flavorings. The dye solution is then added to the first container with mixing.

The product was a clear amber, slightly viscous liquid with a flavor and odor characteristic of spearmint.

EXAMPLE 3

The following ingredients were incorporated into the analgesic maximum strength gel formulation of the invention.

| Ingredients | Weight % | Grams Per 2 Kg |
|---|---|---|
| Part 1 | | |
| PEG 400, USP | 42.8 | 400.0 |
| Glycerin 96% USP | 8.62 | 400.0 |
| Propylene Glycol | 17.2 | 200.0 |
| Saccharin | 9.216 | 5.0 |
| Carbomer 934P | 1.94 | 45.0 |
| Benzocaine, USP | 17.2 | 400.0 |
| Part II | | |
| Methylparaben, USP | 0.172 | 4.0 |
| Phenylcarbinol | 0.431 | 10.0 |
| Spearmint Flavor | 1.72 | 40.0 |
| Part III | | |
| PBG 400, USP | 10.0 | 200.0 |
| FD & C Blue #1 | 0.000086 | 0.0020 |
| D & C Yellow #10 | 0.00414 | 0.0960 |
| FD & C Red #40 | 0.00414 | 0.0960 |
| Part IV | | |
| PEG 400, USP | | QS to 2000 ml |

The ingredients were mixed in accordance with the following procedure in a 2 kilogram jacketed Hobart bowl with a T-line mixer with a 2 inch blade and a stir bar plate.

Into the bowl were placed 400 grams of PEG 400, the glycerin (96%) and the propylene glycol and mixed at low speed until uniform. The mixture was heated to 75°–80° C. with steam, the saccharin was added as dissolved, and the mixture cooled to 55° C. The benzocaine and the carbomer were dry blended in a plastic bag and then added to the bowl with mixer at high speed to pull powders into the vortex. The sides were scraped regularly and a temperature of 60–65° C. was maintained. After 3.5 hours, the carbomer was completely dissolved and the methylparaben and phenylcarbinol was added and dissolved.

Into 400 ml beaker equipped with a bar/plate were added the coloring dyes and the resulting solution was added to the main batch with mixing until uniform then PEG 400 was added QS to 2000 ml in the main batch.

The product was a clear reddish-brown gel with an odor and taste characteristic of spearmint.

EXAMPLE 4

The following ingredients were incorporated into the analgesic regular strength gel formulation of the invention.

| Ingredients | Weight % | Grams Per 2 kg. |
|---|---|---|
| Part 1 | | |
| PEG 400 NF | 50.6 | 1012. |
| Propylene Glycol | 8.62 | 172.4 |
| Glycerin | 17.2 | 344. |
| Saccharin NF Powder | 0.216 | 4.32 |
| Carbomer 934P | 1.94 | 38.8 |
| Benzocaine | 9.08 | 181.6 |
| Part II | | |
| Methylparaben | 0.172 | 3.44 |
| Phenylcarbinol | 0.431 | 8.62 |
| Spearmint Flavor | 1.72 | 34.4 |
| Part III | | |
| PEG 400 NF | 10.0 | 200.0 |
| D & C Red #33 | 0.000950 | 0.0190 |
| FD & C Yellow #6 | 0.00100 | 0.0200 |
| FD & C Blue #1 | 0.0000600 | 0.0012 |
| D & C Yellow #10 | 0.00250 | 0.0500 |
| | 100% | 2000 |

The ingredients were mixed essentially in accordance with the procedure of Example 3. The product was a clear orangish brown soft gel with a mint odor and taste.

The alkanol free glycol based oral analgesic compositions of the invention are surprisingly resistant to microbiological degradation due to the unique preservative agent combination of methylparaben and phenylcarbinol. For example, the preservative agent was efficacious in testing in accordance with an adaptation of the USP methods for inoculating test organisms showing no growth for 28 days.

The five organisms used as test organisms were those listed in the USP as follows:

| | |
|---|---|
| *Escherichia coli* | ATCC #8739 |
| *Staphylococcus aurens* | ATCC #6538 |
| *Pseudomonas aeruginosa* | ATCC #9027 |
| *Candida albicans* | ATCC #10231 |
| *Aspergillus niger* | ATCC #16404 |

In order to determine the efficacy of the preservation agents at lower concentrations additional samples were prepared corresponding to Examples 1 and 3 in which the preservation agent concentrations were 50% and 75% of the corresponding examples.

Accordingly three samples corresponding to Example 1 were prepared with the same proportions of ingredients as Example 1 except that the proportions of methylparaben and phenylcarbinol were each reduced by 25% in one sample, by 50% in the second sample, and by 75% in the third sample, the reduction in weight being replaced with PEG-400 in each instance.

Similarly three samples corresponding to Example 3 were prepared with the same proportions of ingredients as in Example 3 except that the proportions of methylparaben and phenylcarbinol were each reduced by 25% in one sample, by 50% in the second sample, and by 75% in the third sample, the reduction in weight being replaced with PEG-400 in each instance.

The samples corresponding to Examples 1 and 3 with reduced preservation agent concentrations were tested in accordance with the same procedure as the compositions of Examples 1 and 3 and again the analgesic compositions of the invention were surprisingly resistant to microbiological degradation showing no growth for 28 days.

The compositions of the invention must be anhydrous due to the poor water solubility of the methylparaben and the benzocaine and to provide an environment impervious to microbiological growth.

What is claimed is:

1. An alkanol free anhydrous glycol based oral analgesic composition comprising an analgesia producing amount of benzocaine, a glycol solvent system for the benzocaine in an amount sufficient to dissolve the benzocaine comprising polyethylene glycol, having a molecular weight of about 400 to about 600 and a preservative agent in an amount sufficient to protect against microbiological degradation consisting essentially of a combination of about 0.05% to about 0.2% by weight of methylparaben and about 0.25% to about 0.5% by weight of phenylcarbinol each based on the weight of the total composition.

2. The alkanol free glycol based oral analgesic composition of claim 1 in liquid form wherein, based on the weight of the total composition, the amount of benzocaine is about 5 to about 20% by weight, the amount of glycol solvent system is about 40% to about 80% by weight, the glycol solvent system is composed of about 80% to about 100% by weight, based on the weight of the glycol based solvent system, of polyethylene glycol and about 0% to about 20% by weight of a co-solvent for benzocaine compatible with polyethylene glycol.

3. The alkanol free glycol based oral analgesic composition of claim 1 in gel form additionally containing a thickening agent and a solvent for the thickening agent.

4. The alkanol free glycol based oral analgesic composition of claim 3 wherein, based on the weight of the total composition, the amount of benzocaine is about 5 to about 20% by weight, the amount of glycol solvent system is about 40% to about 60% by weight, the glycol solvent system is composed, based on the weight of the glycol based solvent system, of about 80% to about 100% by weight polyethylene glycol and about 0% to about 20% by weight of a co-solvent for benzocaine compatible with polyethylene glycol, the amount of thickening agent is about 2% to about 2.5% by weight and the solvent for the thickening agent is about 16% to about 24% by weight.

5. The alkanol free glycol based oral analgesic composition of claim 4 wherein the polyethylene glycol has a molecular weight of about 400 to about 600, the thickening agent is a carboxy-vinyl polymer and the solvent for the thickening agent is glycerin.

6. The alkanol free glycol based oral analgesic composition of claim 2 wherein the polyethylene glycol has a molecular weight of about 400 to about 600.

7. The alkanol free glycol based oral analgesic composition of claim 5 wherein the co-solvent for benzocaine compatible with polyethylene glycol is propylene glycol.

8. The alkanol free glycol based oral analgesic composition of claim 5 wherein the co-solvent for benzocaine compatible with polyethylene glycol is glycerine.

9. The alkanol free glycol based oral analgesic composition of claim 6 wherein the co-solvent for beinzocaine compatible with polyethylene glycol is propylene glycol.

10. The alkanol free glycol based oral composition of claim 6 wherein the co-solvent for benzocaine compatible with polyethylene glycol is glycerine.

* * * * *